(12) United States Patent
Saksena et al.

(10) Patent No.: US 6,532,378 B2
(45) Date of Patent: Mar. 11, 2003

(54) PULMONARY ARTERY CATHETER FOR LEFT AND RIGHT ATRIAL RECORDING

(75) Inventors: Sanjeev Saksena, Green Brook, NJ (US); Joseph C. Griffin, III, Atco, NJ (US)

(73) Assignee: EP MedSystems, Inc., West Berlin, NJ (US)

( * ) Notice: Subject to any disclaimer, the term of this patent is extended or adjusted under 35 U.S.C. 154(b) by 0 days.

(21) Appl. No.: 09/761,056

(22) Filed: Jan. 16, 2001

(65) Prior Publication Data

US 2001/0031987 A1 Oct. 18, 2001

Related U.S. Application Data

(60) Provisional application No. 60/176,428, filed on Jan. 14, 2000.

(51) Int. Cl.$^7$ .............................. A61B 5/042; A61N 1/04
(52) U.S. Cl. .................. 600/381; 600/374; 607/116; 607/119; 607/122; 607/123
(58) Field of Search .................. 600/374, 381, 600/526; 607/116, 119, 122, 123

(56) References Cited

U.S. PATENT DOCUMENTS

| | | | | |
|---|---|---|---|---|
| 3,995,623 A | * | 12/1976 | Blake et al. ................. | 600/381 |
| 4,721,115 A | * | 1/1988 | Owens ........................ | 600/526 |
| 4,951,682 A | * | 8/1990 | Petre .......................... | 600/522 |
| 5,403,351 A | | 4/1995 | Saksena | |
| 5,443,074 A | * | 8/1995 | Roelandt et al. ............. | 600/526 |
| 5,571,159 A | | 11/1996 | Alt | |
| 5,653,734 A | | 8/1997 | Alt | |
| 5,697,965 A | * | 12/1997 | Griffin, III ................... | 607/123 |
| 6,141,576 A | * | 10/2000 | Littmann et al. ............ | 600/381 |

OTHER PUBLICATIONS

Saksena et al., "Electrophysiology and Endocardial Mapping of Induced Atrial Fibrillation in Patients with Spontaneous Atrial Fibrillation," The American Journal of Cardiology, vol. 83, pp. 187–193, Jan. 15, 1999.

\* cited by examiner

*Primary Examiner*—Lee Cohen
(74) *Attorney, Agent, or Firm*—Norman E. Lehrer

(57) ABSTRACT

A catheter for indirect left atrial mapping from the left pulmonary artery is disclosed. The catheter includes an elongated flexible member with a distal end and a proximal end. Located at the distal end is a balloon and an array of mapping electrodes. Located at the proximal end is a manifold to which various ports are secured. In a second embodiment, the catheter differs from the first embodiment in that interspersed within the array of mapping electrodes are defibrillation electrodes. Also, located proximally of the array of mapping electrodes is an array of defibrillation electrodes. In a third embodiment, the catheter differs from the first embodiment in that five defibrillation electrodes are located between the array of mapping electrodes and the balloon. Located proximally of the array of mapping electrodes is an array of defibrillation electrodes.

12 Claims, 2 Drawing Sheets

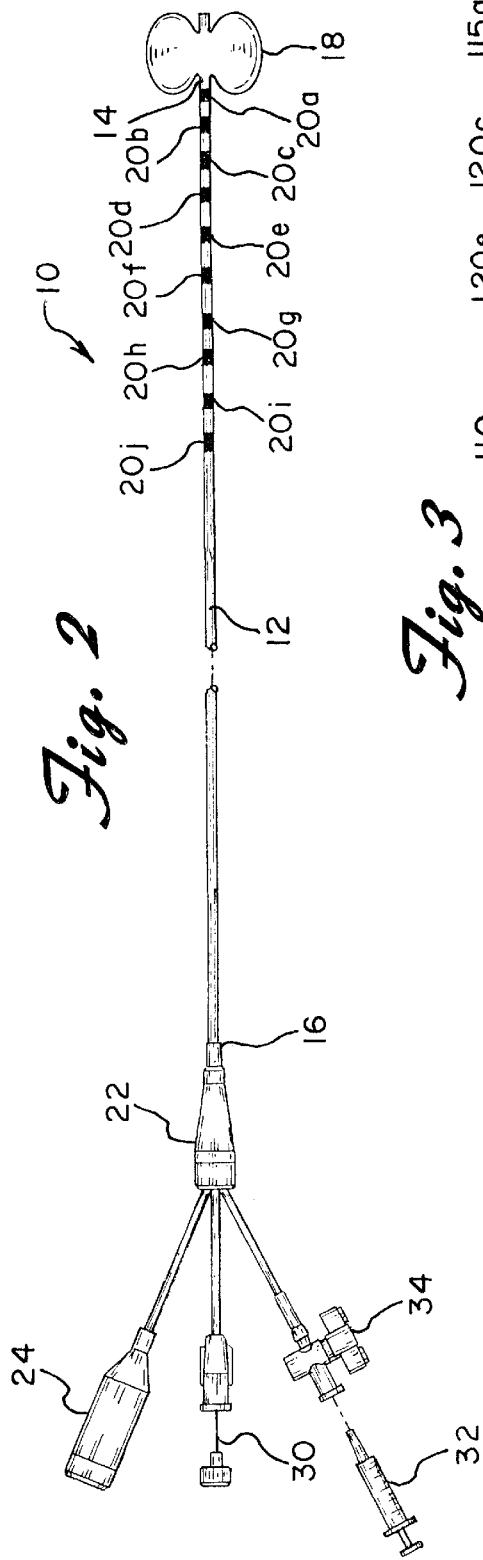
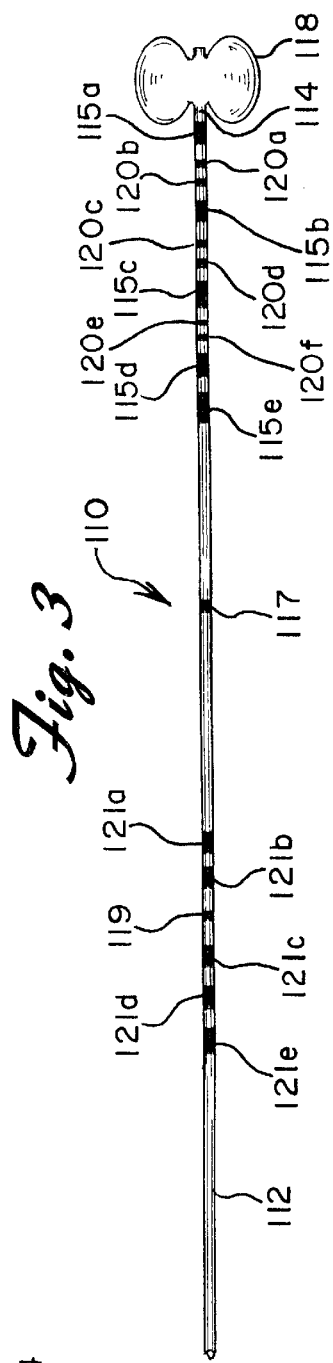
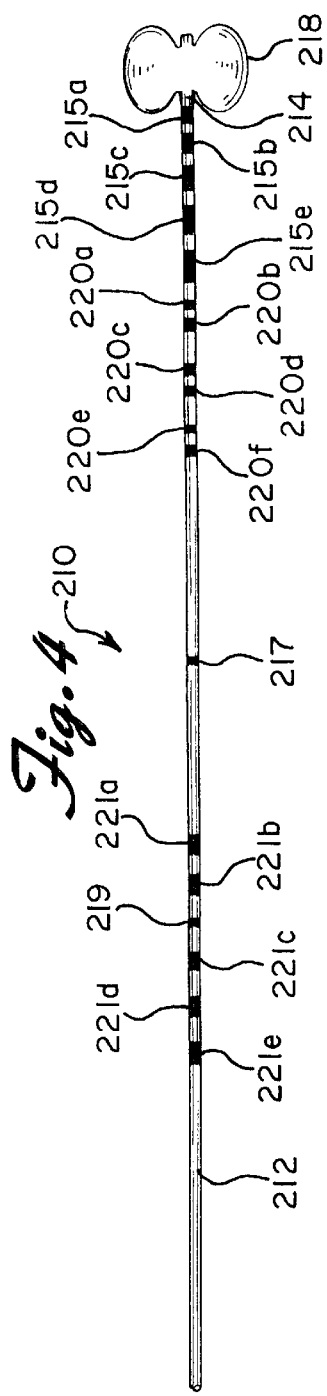

PULMONARY ARTERY CATHETER FOR LEFT AND RIGHT ATRIAL RECORDING

CROSS-REFERENCE TO RELATED APPLICATIONS

This application claims the benefit of U.S. Provisional Patent Application Ser. No. 60/176,428, filed Jan. 14, 2000.

BACKGROUND OF THE INVENTION

The present invention is directed toward a pulmonary artery catheter and more particularly, toward a left pulmonary artery catheter which records activity in the left atrium.

A catheter placed in the pulmonary artery for measuring cardiac pressure, and thermal dilution (for calculating cardiac output) is well known in the art and has been used commercially for more than the last twenty years. More recently, oxygen sensors have been used on the catheter to measure oxygen content of the blood, and even more recently, defibrillation electrodes have been added to a pulmonary artery catheter to aid in cardioversion in patients with atrial or ventricular fibrillation or tachycardia, who are otherwise being monitored by a pulmonary artery catheter.

An atrial cardioversion catheter as disclosed, for example, in U.S. Pat. No. 5,571,159 to Alt contains electrodes in the right atrium for pacing the heart, as well as for recording a ventricular spike on which to trigger the defibrillating shock. A ventricular defibrillation catheter in the pulmonary artery has been described in U.S. Pat. No. 5,403,351 to Saksena.

Pulmonary artery catheters known in the art and which are used today do not embody a plurality of electrodes purposefully placed which could assist in the diagnosis of electrophysiological disorders of the heart, such as the disease of atrial fibrillation.

Atrial fibrillation is a disorganized electrical disorder of the upper chambers of the heart. It was once thought to be a disease of aging, relatively benign, and untreatable. However, the number of people exhibiting this disease is quite large, and the effects of the disease are quite profound. Atrial fibrillation presently affects over 2 million Americans, and this number is increasing with the aging of the population. It is the leading cause of stroke in the U.S.; doubles the mortality from heart disease; and leads to reduced heart function, and hence, a diminished lifestyle and serious morbidity and mortality. Thus, over the last several years, atrial fibrillation is a heart condition which has moved to the forefront in terms of both research, and clinically applied therapies. Research in the area of recording and defining electrophysiological properties and anatomic locations of the tissue generating this atrial arrhythmia has been shown in publications by co-inventor Saksena. (See Am. J. Cardiology 1999, 83:187–193.)

Basic electrophysiological (EP) recording of the heart consists of "mapping" the timing of the activation of the various cells as very low voltage electrical activity conducts through the heart. To do this, various catheters with a plurality of recording electrodes are placed at various locations within the heart. In a basic study, catheters are placed in the high right atrium, the area around the atrial-ventricle node, and the apex of the right ventricle. These placements allow the physician to measure the conduction training from the top of the heart to the bottom, primarily in the right atrium and right ventricle. To measure conduction "crossways", or laterally across the heart, a catheter, generally with ten electrodes, is placed in the coronary sinus, a vessel which goes around the back side of the upper heart.

Recent research has shown that left atrial electrical activity is an important factor in the diagnosis of the origin of atrial fibrillation. Regional atrial mapping of different right and left atrial regions or very "focal" mapping of left sided electrical patterns from inside the atrium is helpful. However, putting a catheter inside the left side of the heart is not easy, and is associated with risk of death or clot formation resulting in stroke or paralysis in patients with or without atrial fibrillation. Thus, keeping catheters out of the cavity of the left atrium is highly desirable and preferred for simplicity of technique. The current methods of puncturing a hole in the septum between atria and inserting a recording catheter inside the left atrium is not routine, is risky, and is fairly undesirable.

SUMMARY OF THE INVENTION

The present invention is designed to overcome the deficiencies of the prior art discussed above. It is an object of the present invention to provide a catheter which has a number of electrodes placed on a pulmonary artery catheter used for the primary purpose of recording atrial activity, and, more specifically, activity of the left atrium, but can also be used for recording activity in the right atrium.

It is another object of the present invention to provide a catheter for atrial mapping and a method of recording regional left atrial activation patterns for spontaneous and induced electrical activity in the heart.

It is a further object of the present invention to provide a catheter for defibrillating or cardioverting the heart.

In accordance with the illustrative embodiments demonstrating features and advantages of the present invention, there is provided a catheter for indirect left atrial mapping from the left pulmonary artery and for mapping the superior interatrial septum, the superior left atrium, and the lateral left atrium. In addition, these recordings can detect early electrical activity in the right and left superior pulmonary veins. Recordings can also be obtained from the right pulmonary artery, the right interatrial septum, and the superior right atrium. The catheter essentially includes an elongated flexible member with a distal end and a proximal end. Located at the distal end is a balloon and an array of mapping electrodes. Located at the proximal end is a manifold to which various ports are attached. The ports may be used, for example, to secure connectors for the electrodes.

In a second embodiment of the present invention the catheter has the same structure as the catheter in the first embodiment but differs in that interspersed within the array of mapping electrodes are defibrillation electrodes. Located proximally of the array of mapping electrodes is an array of defibrillation electrodes and two sense electrodes.

In a third embodiment of the present invention the catheter has the same structure as the catheter in the first embodiment but differs in that an array of defibrillation electrodes are located between the balloon and the array of mapping electrodes. Located proximally of the array of mapping electrodes is an array of defibrillation electrodes and two sense electrodes.

Other objects, features, and advantages of the invention will be readily apparent from the following detailed description of preferred embodiments thereof taken in conjunction with the drawings.

BRIEF DESCRIPTION OF THE DRAWINGS

For the purpose of illustrating the invention, there are shown in the accompanying drawings forms which are presently preferred; it being understood that the invention is not intended to be limited to the precise arrangements and instrumentalities shown.

FIG. 2 is a perspective view of the catheter of a first embodiment of the present invention;

FIG. 3 is a perspective view of a second embodiment of the present invention; and FIG. 4 is a perspective view of a third embodiment of the present invention.

DETAILED DESCRIPTION OF THE PREFERRED EMBODIMENT

Figure 1:
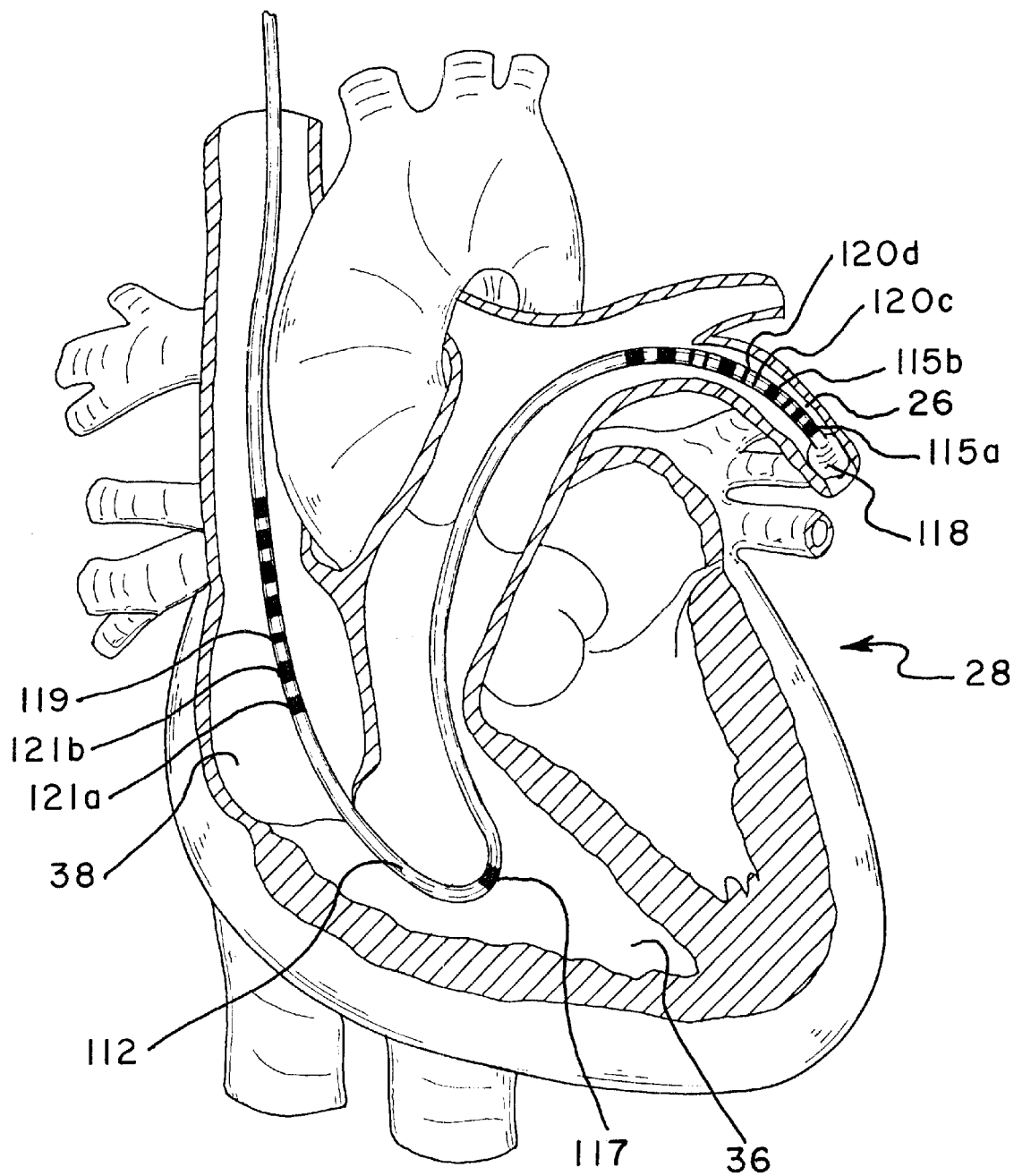
FIG. 1 illustrates the present invention placed within a patient's heart.

Referring now to the drawings in detail wherein like reference numerals have been used throughout the various figures to designate like elements, there is shown in FIG. 2 a catheter constructed in accordance with the principles of the present invention and designated generally as 10.

A first embodiment of the catheter 10 of the present invention essentially includes a flexible elongated member 12 with a distal end 14 and a proximal end 16. (See FIG. 2.) A balloon 18 is attached at the distal end 14 of the elongated member 12. The balloon 18 extends for approximately 15 mm. A preferred material for producing the flexible member is extruded polyether block amide of the type sold by Atcochem North America, Inc. under the trademark PEBAX. However, the flexible member may be comprised of other polymeric materials which have excellent memory characteristics such as polyurethane, silicone rubber, and plasticized PVC etc.

An array of electrodes 20a–20j is placed on the distal end 14 of the elongated member 12, proximal the balloon 18. (See FIG. 2.) The electrodes 20a–20j are spaced approximately 2 mm apart from each other and each electrode extends approximately 2 mm in length. The array extends for approximately 38 mm of the elongated member 12. Electrical wires (not shown) from the electrodes pass through the interior of the flexible member 12 to a manifold 22 secured to the proximal end 16 of the elongated member 12. Each electrode is coupled to its own connector, which is shown, for example, at 24, and is ultimately connected to recording equipment located near the proximal end 16 of the elongated member 12. The distal end 14 of the elongated member 12, including the balloon 18 and electrodes 20a–20j, is inserted into the left pulmonary artery 26 of a patient's heart 28 when in use. (See FIG. 1.) The electrodes 20a–20j sense electrical activity of the heart at certain locations and the resulting activity is recorded. Various ports are secured to the manifold. These ports may be used, for example, to introduce a guidewire 30 into the catheter, to attach an inflation mechanism for inflating the balloon, or to attach a syringe 32 with a stopcock 34 which may be used to introduce various solutions into the catheter. (See FIG. 2.)

The connector for the electrodes would preferably be a multi-pin connector, enabling the catheter to have only one connector for all of the recording electrodes. Such connectors can be connected to an extension cable with one connect or on the catheter connecting end, and several pin type connectors on the recorder connecting end.

The catheter may also have incorporated therein defibrillation electrodes. The recording electrodes can be placed distally, proximally, or inter-spaced among the defibrillation electrodes. The current electrodes could be made of stainless steel, platinum, or other electrode material, such as thin flexible electrodes or any other electrode material known in the art.

For example, a second embodiment of the present invention with defibrillation electrodes is shown in FIG. 3. The catheter 110 described in this embodiment is similar in structure and function to the catheter described in the first embodiment. The differences between the two embodiments are discussed herein.

In the second embodiment a balloon 118 is located at the distal end 114 of the elongated member 112 which extends for 15 mm, as described in the first embodiment. Five defibrillation electrodes 115a–115e are located at the distal end 114 of the elongated member 112. Interspersed among the defibrillation electrodes 115a–115e are three mapping electrode pairs 120a–120f. The array of electrodes 115a–115e and 120a–120f extends for approximately 72 mm of the elongated member 112. The defibrillation electrodes 115a–115e are each approximately 5 mm in length and are spaced approximately 14 mm apart from each other, with one of the electrodes 115e spaced 5 mm from the defibrillation electrode 115d closest to it. Each mapping electrode 120a–120f is approximately 2 mm in length. The distance between each electrode in the pair is 2 mm.

Located proximally of the mapping and defibrillation electrodes is a sense electrode 117. The sense electrode 117 is approximately 2 mm in length. This electrode is located in the right ventricle 36 when the catheter is placed within a patient's heart. Located proximally of the sense electrode 117 is a sense electrode 119 and five defibrillation electrodes 121a–121e which are placed within the right atrium 38 of a patient's heart. The sense electrode 119 extends for approximately 2 mm and each defibrillation electrode 121a–121e extends for approximately 5 mm and is spaced 5 mm apart from each other. The electrode array 121a–121e extends for approximately 52 mm.

A third embodiment of the present invention is shown in FIG. 4. The catheter 210 described in this embodiment is similar in structure and function to the catheter described in the first embodiment. The differences between the two embodiments are discussed herein.

In the third embodiment, there is a balloon 218 located at the distal end 214 of the elongated member 212 which extends for 15 mm, as described in the first embodiment. Five defibrillation electrodes 215a–215e are located at the distal end 214 of the elongated member 212. Located proximally of the electrodes 215a–215e are three mapping electrode pairs 220a–220f. The array of defibrillation and mapping electrodes 215a–215e and 220a–220f extends for approximately 78 mm of the elongated member. The defibrillation electrodes are each 5 mm in length and are spaced 5 mm apart from each other. Each mapping electrode is 2 mm in length. The distance between each electrode in the pair is 2 mm and the distance between each pair is 5 mm.

Located proximally of the mapping and defibrillation electrodes is a sense electrode 217. The sense electrode 217 is approximately 2 mm in length and is located in the right ventricle 36 when the catheter is placed within a patient's heart. Located proximally of the sense electrode 217 and in the right atrium 38 is a sense electrode 219 and five defibrillation electrodes 221a–221e. The sense electrode 219 extends for approximately 2 mm and each defibrillation electrode 221a–221e extends for approximately 5 mm and are spaced 5 mm apart from each other. This electrode array extends for approximately 52 mm.

In use the catheter is inserted into and guided through the heart as shown in FIG. 1 so that the distal end of the catheter with the mapping electrodes thereon is positioned within the left pulmonary artery. In this position, indirect left atrial mapping can be obtained in addition to mapping the superior interatrial septum, the superior left atrium, and the lateral left atrium is possible. In addition, these recordings can detect early electrical activity in the right and left superior pulmonary veins. Recordings can also be obtained from the right pulmonary artery, the right interatrial septum, and the superior right atrium.

The present invention may be embodied in other specific forms without departing from the spirit or essential attributes thereof and accordingly, reference should be made to the appended claim rather than to the foregoing specification as indicating the scope of the invention.

We claim:

1. A left pulmonary artery catheter for mapping activity in the left atrium comprising:

an elongated flexible member having a proximal end and a distal end;

a balloon located at said distal end of said flexible member;

an array of mapping electrodes located at said distal end of said elongated member and proximally of said balloon, said array including three pairs of electrodes; and five defibrillation electrodes interspersed among said pairs of mapping electrodes.

2. The left pulmonary artery catheter for mapping activity in the left atrium of claim 1 wherein each of said mapping electrodes is spaced two millimeters apart from each other.

3. The left pulmonary artery catheter for mapping activity in the left atrium of claim 1 wherein an array of defibrillation electrodes is located proximally of said array of mapping electrodes.

4. A left pulmonary artery catheter for mapping activity in the left atrium comprising:

an elongated flexible member having a proximal end and a distal end;

a balloon located at said distal end of said flexible member;

an array of mapping electrodes located at said distal end of said elongated member and proximally of said balloon, said array including three pairs of electrodes; and five defibrillation electrodes located distally of said array of mapping electrodes.

5. The left pulmonary artery catheter for mapping activity in the left atrium of claim 4 wherein an array of defibrillation electrodes is located proximally of said array of mapping electrodes.

6. A method for mapping activity in the left atrium of a patient's heart comprising the steps of:

providing an elongated flexible member having a proximal end and a distal end; a balloon located at said distal end of said flexible member; and an array of mapping electrodes located at said distal end of said elongated member and proximal of said balloon;

inserting said distal end of said flexible member within said left pulmonary artery wherein said array of electrodes is located within the left pulmonary artery, and analyzing electrical signals obtained from said array of mapping electrodes located within the left pulmonary artery.

7. The method for mapping activity in the left atrium of a patient's heart of claim 6 wherein each of said mapping electrodes is spaced two millimeters apart from each other.

8. The method for mapping activity in the left atrium of a patient's heart of claim 6 wherein said array of mapping electrodes includes three pairs of electrodes.

9. The method for mapping activity in the left atrium of a patient's heart of claim 8 wherein five defibrillation electrodes are interspersed among said pairs of mapping electrodes.

10. The method for mapping activity in the left atrium of a patient's heart of claim 9 wherein an array of defibrillation electrodes is located proximally of said array of mapping electrodes and said array of defibrillation electrodes is adapted to be inserted within the right atrium of the patient's heart.

11. The method for mapping activity in the left atrium of a patient's heart of claim 8 wherein five defibrillation electrodes are located distally of said array of mapping electrodes.

12. The method for mapping activity in the left atrium of a patient's heart of claim 11 wherein an array of defibrillation electrodes is located proximally of said array of mapping electrodes.

* * * * *